United States Patent [19]

Williams et al.

[11] 4,210,459

[45] Jul. 1, 1980

[54] POLYMER COMPOSITE ARTICLES CONTAINING POLYSULFIDE SILICON COUPLING AGENTS

[75] Inventors: Thomas C. Williams, Ridgefield, Conn.; George E. Totten, West Haverstraw, N.Y.

[73] Assignee: Union Carbide Corporation, New York, N.Y.

[21] Appl. No.: 1,856

[22] Filed: Jan. 8, 1979

Related U.S. Application Data

[62] Division of Ser. No. 810,853, Jun. 28, 1977, Pat. No. 4,151,157.

[51] Int. Cl.$^2$ .............................................. C09C 3/12
[52] U.S. Cl. ............................... 106/308 N; 428/391; 428/405
[58] Field of Search ............. 106/308 NQ; 260/42.15; 428/405, 391

[56] References Cited

U.S. PATENT DOCUMENTS

| | | | |
|---|---|---|---|
| 3,768,537 | 10/1973 | Hess et al. | 260/42.15 |
| 3,842,111 | 10/1974 | Meyer-Simon et al. | 260/448.2 E |
| 3,873,489 | 3/1975 | Thurn et al. | 260/33.6 AQ |
| 3,997,356 | 12/1976 | Thurn et al. | 106/308 Q |
| 4,000,347 | 12/1976 | Ronney et al. | 260/448.2 N |
| 4,044,037 | 8/1977 | Mui et al. | 260/448.2 N |
| 4,099,981 | 7/1978 | Mui et al. | 106/308 Q |

*Primary Examiner*—James Poer
*Attorney, Agent, or Firm*—Richard J. Gallagher

[57] ABSTRACT

Polymer composites, such as rubber, thermoset and thermoplastic articles, comprising the reaction product of (a) an organic polymer, (b) an inorganic substrate and (c) a polysulfide silicon coupling agent, and articles comprising an inorganic substrate treated with a polysulfide silicon coupling agent.

15 Claims, No Drawings

POLYMER COMPOSITE ARTICLES CONTAINING POLYSULFIDE SILICON COUPLING AGENTS

BACKGROUND OF THE INVENTION

This invention relates to novel polymer composite articles of manufacture comprising the reaction product of (a) an organic polymer (b) an inorganic substrate and (c) a polysulfide silicon coupling agent, as well as to articles of manufacture comprising an inorganic substrate treated with a polysulfide silicon coupling agent.

The use of various silicon coupling agents to enhance the adhesion of various inorganic substrates with a broad variety of organic polymers to promote coupling and bonding therewith is well known in the art. Note for example, U.S. Pat. Nos. 2,832,754; 2,971,864; 3,258,477; 3,661,628; 3,671,562; 3,705,911; 3,706,592; 3,754,971; and 4,000,347; and the like. Thus, as is conventionally understood in the art the silicon coupling agent serves as a crosslinker that is chemically or physically bonded to both the inorganic substrate and the organic polymer in the polymer composite.

SUMMARY OF THE INVENTION

Accordingly, it is an object of this invention to provide polymer composite articles of manufacture comprising the reaction product of (a) an organic polymer, (b) an inorganic substrate and (c) a novel polysulfide silicon composition of matter as disclosed in the concurrently filed U.S. application Ser. No. 810,785, entitled "POLYSULFIDE SILICON COMPOUNDS" (D-10614) by T. C. Williams and G. E. Totten. It is another object of this invention to provide articles of manufacture comprising an inorganic substrate treated with said novel polysulfide substituted silicon compositions of matter. Other objects and advantages of this invention will become readily apparent from the following description and appended claims.

More specifically then, one embodiment of this invention relates to a polymer composite article of manufacture comprising the reaction product of (a) an organic polymer, (b) an inorganic substrate, and (c) polysulfide substituted silicon coupling agent selected from the class consisting of (i) polysulfide substituted silane compounds having the formula

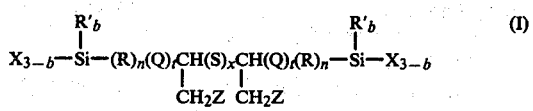

wherein R' is a monovalent radical selected from the class consisting of hydrogen, hydrocarbon radicals and substituted hydrocarbon radicals;

wherein X is a hydrolyzable radical selected from the class consisting of alkoxy, aryloxy, acyloxy, secondary amino and aminooxy radicals;

wherein R is a divalent bridging group selected from the class consisting of hydrocarbon radicals, groups of the formula —R"OR"— and groups of the formula —R"SR"— wherein R" is a divalent hydrocarbon radical;

wherein Q is an oxygen atom or a sulfur atom;

wherein Z is a monovalent organic amino radical the nitrogen atom of which is directly bonded to the carbon atom of the (CH₂) group of the above formula;

wherein n has a value of 0 or 1 and t has a value of 0 or 1, with the proviso that when n is 0, then t is 0; and wherein b has a value of 0 to 2, and x has a value of 2 to 4;

(ii) Polysulfide siloxanes consisting essentially of siloxy units having the formula

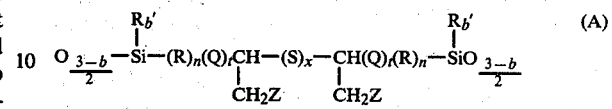

wherein R', R, Q, Z, n, t, b and x are the same as defined above; and (iii) polysulfide siloxane copolymers consisting essentially of at least one siloxy unit represented by formula (A) above and at least one siloxy unit represented by the formula

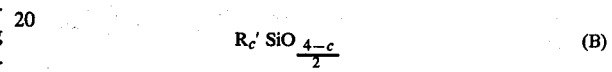

wherein R' is the same as defined in formula (A) above and wherein c has a value of from 0 to 3 inclusive.

DESCRIPTION OF THE PREFERRED EMBODIMENTS

The polymer composite articles of manufacture of this invention can correspond to any heretofore conventional polymer composite comprising an organic polymer bonded to an inorganic substrate through the use of conventional silicon coupling agents, the difference being that the polymer composite articles of manufacture of this invention employ as the coupling agent, the above referred to polysulfide silicon compositions of matter. Thus, the polymer composite articles of manufacture of this invention include such conventional articles as rubber, thermoplastic and thermosetting resins, paints, varnishes, inks and the like.

The organic polymer components of the novel composites of this invention as well as methods for their preparation are well known in the art and include a wide variety of polymers. Illustrative examples of such polymers, either singularly or in adjuncture with each other include any of the homopolymers and copolymers of olefinic and diolefinic monomers such as ethylene, propylene, butylenes, methylpentenes, styrene ring substituted styrenes, alphamethyl styrene, vinyl chloride, vinyl fluoride, vinyllidene chloride, acrylonitrile, methacryhonitrile, vinyl alcohol esters, acrylic acid and its esters and amides, methacrylic acid and its esters and amides, allyl phthalate esters, butadiene, isoprene, chloroprene, ethylidene, norbornene, 1,5-hexadiene, divinyl benzenes and the like, as well as synthetic condensation polymers commonly classed as alkyl resins, polyesters, nylons, phenolics, epoxides polysulfones, polysulfonamides, polysulfides, polyurethanes, polyureas and the like, as well as oligomers and polymers derived from plant and animal sources such as cellulose esters and ethers, carbon-carbon unsaturated fatty acid triglycerides and natural hevea and ficus rubbers and the like.

The more preferred organic polymers employable in this invention are the conventional thermoplastic forming resins, thermoset forming resins, and rubber forming polymers. Illustrative of some of the more preferred thermoplastic forming resins include, e.g. polyethylene, polypropylene, polystyrene, polyvinylchloride, polyvinyl butyral, nylon, polyacrylonitrile, polycarbonates, polyesters, and the like as well as copolymers and terpolymers thereof. Illustrative of some of the more preferred thermoset forming resins include, e.g. unsaturated polyesters, epoxides, phenolics, melamine, and the like.

The more preferred organic polymers employable in this invention are the conventional vulcanizable unsaturated rubber polymers used to prepare vulcanizable rubber compounds. Illustrative of such vulcanizable rubber polymers are natural rubber and synthetic rubber polymers as disclosed, e.g. in *The Elastomer Manual* (1972 Edition) published by International Institute of Synthetic Rubber Producer, Inc., such as styrene-butadiene rubber polymers, butadiene rubber polymers, ethylenepropylene rubber terpolymers, chloroprene rubber polymers, nitrile rubber polymers, bromo- and chloro- butyl rubber polymers, polyisoprene rubber polymers, and the like. Especially preferred are the conventional sulfur vulcanizable rubber polymers such as natural rubber, styrene-butadiene rubber polymers, butadiene rubber polymers, and polyisoprene rubber polymers.

The inorganic substrates employable in this invention are well known in the art and include any conventional inorganic substrate generally employed in rubber, thermoplastic and thermosetting resins, paints varnishes, inks and the like, and which are substantially reactive toward the polysulfide silicon coupling agents employed in this invention. Illustrative examples of such inorganic substrates include such reinforcing materials, pigments or fillers such as siliceous materials such as plate glass, glass fibers, asbestos, sand, clay, talc, silica, e.g. hydrated silica, precipitated silica, fumed silica, silica aerogels and silica xero-gels, metal silicates, e.g. aluminum silicate, calcium silicate, calcium, metasilicate, magnesium silicate, feldspar, concrete, ceramic materials and the like; metals such as aluminum, copper, cadmium, chromium, magnesium, nickel, silver, tin, titanium, zinc, and the like; the alloys of such metals as brass, bronze, steel, and the like including metals which have been surface treated with phosphates, chromates, and the like; metal oxides such as aluminum oxide, iron oxides, lead oxides, titanium dioxide, zinc oxide and the like. Of course, it is understood that the particular configuration of the inorganic substrate employed is not critical and that the inorganic materials can be in any various form such as sheets, plates, blocks, wires, cloth, fibers, filaments, particules, powders and the like. The preferred inorganic substrates are the siliceous materials, especially silica and metal silicate fillers or pigments.

The polysulfide silicon compositions of matter employable in this invention are those polysulfide substituted silanes and siloxanes disclosed in the concurrently filed U.S. application Ser. No. 810,785. entitled "POLYSULFIDE SILICON COMPOUNDS" (D-10,614) by T. C. Williams and G. E. Totten, the disclosure of which is encompassed herein by reference thereto.

More specifically such polysulfide silicon compositions of matter include polysulfide silane compounds having the formula:

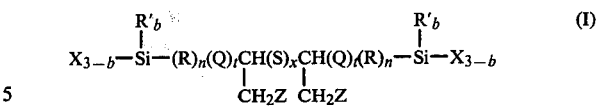

wherein R', R, Q, Z, X, t, n, b and x are the same as defined above.

DESCRIPTION OF THE PREFERRED EMBODIMENTS

Illustrative radicals represented by R' in formula (I) above are hydrogen and monovalent hydrocarbon radicals which can contain from 1 to 20 carbon atoms, which are unsubstituted or substituted with substitutes which are inert under the reaction conditions employed in preparing the silane compounds of this invention. Such hydrocarbon radicals include straight and branched chain alkyl radicals (e.g. methyl, ethyl, n-propyl, isopropyl, n-butyl, isobutyl, t-butyl, n-pentyl, n-hexyl 2-ethylhexyl, n-decyl, dodecyl, n-tetradecyl, n-hexadecyl, n-octadecyl, eicosyl and the like); alkenyl radicals (e.g. vinyl, allyl, 2,4-hexadienyl, 9, 12, 15-octadecatrienyl, and the like); cycloalkyl radicals (e.g. cyclopentyl, cyclohexyl, and the like); cycloalkenyl radicals (e.g. 3-cyclohexenyl and the like); aryl radicals (e.g. phenyl, naphthyl, biphenyl, and the like); aralkyl radicals (e.g. p-methylphenyl, p-cyclohexylphenyl, alphamethylnaphthyl, and the like); haloaryl radicals (e.g. 4-chlorophenyl, 2,4-dichlorophenyl, chloronaphthyl, and the like); nitroaryl radicals (e.g. 4-nitrophenyl, and the like); cyanoalkyl radicals (e.g. beta-cyanoethyl, gammacyanopropyl, and the like). Of course, it is understood that each R' radical can be the same or different in any given silane compound. Preferably R' is hydrogen or a monovalent unsubstituted hydrocarbon radical. More preferably R' is an alkyl radical containing from 1 to 18 carbon atoms and most preferably from 1 to 8 carbon atoms.

Illustrative hydrolyzable radicals represented by X in formula (I) above include alkoxy radicals (e.g. methoxy, ethoxy, propoxy, isopropoxy, 2-methoxyethoxy, dodecyloxy, betacyanoethoxy, and the like); aryloxy radicals (e.g. phenoxy, and the like); acyloxy radicals (e.g. formyloxy, acetoxy, and the like); secondary amino radicals such as dialkylamino (e.g. dimethylamino, diethylamino and the like) and aminooxy radicals such as dialkylaminooxy (e.g. diethylaminooxy and the like); Of course, it is understood that each X radical can be the same or different in any given silane compound, although normally it is preferred that each X be the same. Preferably X is an alkoxy radical, especially alkoxy radicals selected from the group consisting of methoxy, ethoxy, and 2-methoxyethoxy.

Illustrative divalent bridging radicals represented by R in formula (I) above include hydrocarbon radicals, oxygen containing hydrocarbon radicals (i.e. —R'-'OR"—) and sulfur containing hydrocarbon radicals (i.e. —R"SR"—). Normally, such radicals contain from 1 to 12 carbon atoms. Illustrative divalent hydrocarbon radicals represented by R include alkylene radicals (e.g. methylene (—CH$_2$—), ethylene, propylene, isopropylene, butylene, neopentylene, pentylene, 2-ethylhexylene, dodecylene, and the like); arylene radicals (e.g. phenylene, and the like); arylene containing alkylene radicals (e.g. methylenephenylene —(CH$_2$C$_6$H$_4$—), and the like); and the like. The oxygen containing hydrocarbon radicals represented by R are those of the formula —R"OR"— wherein R" is a divalent hydrocarbon radical such as alkyleneoxyalkylene radicals (e.g. ethyleneoxymethylene (—C$_2$H$_4$OCH$_2$—), propyleneoxymethylene (—CH$_2$CH$_2$CH$_2$O—CH$_2$—), ethyleneoxyethylene (—C$_2$H$_4$OC$_2$H$_4$—), propyleneoxyethylene (—C$_3$H$_6$OC$_2$H$_4$—), propyleneoxypropylene (—C$_3$H$_6$OC$_3$H$_6$—), and the like); aryleneoxyalkylene radicals (e.g. phenyleneoxymethylene (—C$_6$H$_4$OCH$_2$—), and the like); and the like. The sulfur (or thio) containing hydrocarbon radicals represented by R are those of the formula —R"SR"— wherein R" is a divalent hydrocarbon radicals such as alkylenethioalkylene radicals (e.g. ethylenethiomethylene (—C$_2$H$_4$SCH$_2$—), propylenethiomethylene (—CH$_2$CH$_2$CH$_2$SCH$_2$—), propylenethioethylene (—C$_3$H$_6$SC$_2$H$_4$—), propylenethiopropylene (—C$_3$H$_6$SC$_3$H$_6$—), and the like); arylenethioalkylene radicals (e.g. phenylenethiomethylene (—C$_6$H$_4$SCH$_2$—), and the like); and the like. Preferably R is an alkyleneoxyalkylene radical wherein each divalent alkylene radical contains from 1 to 3 carbon atoms, the most preferred R bridging group being propyleneoxymethylene (—CH$_2$CH$_2$CH$_2$OCH$_2$—).

As pointed out above, when n has a value of 0, then t has a value of 0 and the silicon atom is directly bonded to the carbon atom of the (CH) group in formula (I) above. However, when n has a value of 1, then t can have a value of 0 or 1. The preferred silanes of formula (I) above are those wherein b has a value of 0 and n has a value of 1.

The monovalent organic amino radicals represented by Z in above formula (I) include any organic amino radical derived by removing a hydrogen atom from the nitrogen atom of a corresponding organic primary or secondary amine employed in the preparation of the amino substituted mercapto organosilane compounds used to prepare the polysulfide silanes employable in this invention as explained more fully below. Thus, illustrative monovalent organic amino radicals represented by Z in formula (I) include the corresponding organic amino radicals derived by removing a hydrogen atom from the nitrogen atom of such amines as ethylamine, dimethylamine, diethylamine, di-n-butylamine, sec-butylamine, n-octylamine, 2-hydroxyethylamine, bis-(2-hydroxyethyl)amine, 2-methoxyethylamine, 3-hydroxypropylamine, aniline, ortho and para toluidines, ortho and para aminophenols, p-anisidine, p-dimethylaminoaniline, o- and p-chloroanilines, p-acetamidoaniline, benzylamine, o-mercaptoaniline, m-aminophenyltrimethoxysialne, 2-aminopyridine, 5-amino-2-mercaptobenzothiazole, cyclohexylamine, cyclohexylmethylamine, N-methylaniline, 2-naphthylamine, ethylenediamine, diethylene triamine, p-phenylenediamine, oxydianiline, 2-mercaptoethylamine, allylamine, 3-aminocrotononitrile, piperonylamine, piperazine, piperidine, morpholine, 3-(phenylamino)propyltrimethoxysilane, p-aminodiphenylamine, 3-(n-butylamino)propoxytrimethoxysilane, and the like.

Alternatively, then the organic amino radicals represented by Z as discussed above may be those of the formula —NZ$^1$Z$^2$ wherein Z$^1$ is an organic radical and Z$^2$ is hydrogen or an organic radical when Z$^1$ and Z$^2$ are taken individually, and when Z$^1$ and Z$^2$ are taken together with the nitrogen atom of the above formula they form a heterocyclic radical.

Accordingly, the more preferred polysulfide silane compounds employable in this invention are those having the formula

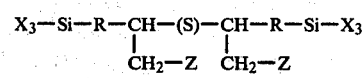

wherein X is a hydrolyzable radical as defined above, especially an alkoxy radical such as methoxy, wherein R is a divalent alkylene or alkyleneoxyalkylene bridging radical as defined above, especially alkyleneoxyalkylene radicals, such as propyleneoxymethylene and wherein Z is an organic amino radical as defined above, especially an amino radical of the formula —NZ$^1$Z$^2$, wherein Z$^1$ and Z$^2$ are taken individually and Z$^1$ is an organic radical selected from the class consisting of alkyl, aryl, aralkyl and alkaryl with substituent radicals which do not adversely affect the preparation of the silane compounds of this invention, such as hydroxy, alkoxy, mercapto, amino (e.g. —NH$_2$, N(CH$_3$)$_2$, NHC$_6$H$_5$, NHC$_2$H$_4$N(CH$_3$)$_2$ and the like) and hydrolyzable silyl (e.g. —Si(OCH$_3$)$_3$) substituted alkyl, aryl, aralkyl and alkaryl radicals, haloaryl (e.g. 4-chlorophenyl, etc.) radicals and the like, and wherein Z$^2$ is hydrogen or a Z$^1$ radical as defined above, and wherein x has a value of 2 to 4.

The polysulfide silanes employable in this invention can be conveniently prepared by heating the novel amino substituted mercapto organosilanes disclosed in concurrently filed U.S. Application No. 810,840 (D-9978) entitled "AMINO SUBSTITUTED MERCAPTO ORGANOSILICON COMPOUNDS" by T. C. Williams and G. E. Totten in the presence of elemental flowers of sulfur, the entire disclosure of which is incorporated herein by reference thereto. The amino-catalyzed addition of organic mercaptans to elemental sulfur is well known in the art as seen e.g. by Vineyard, B. D.; "J. Organic Chemistry" 31 p. 601 (1966) and 32, p. 3833 (1967) and this reaction can be used to prepare the polysulfide silanes employable in this invention, the basic substituent amino group on the starting amino substituted mercapto organosilanes allowing the reaction to be autocatalytic. Thus, the process factors involved in forming the polysulfide silanes are not critical. Said process basically involves merely refluxing two moles of the amino substituted mercapto organosilane in the presence of flowers of sulfur and in the further presence or absence of an organic solvent until the desired polysulfide silane is produced. Generally, it is preferred to carry out the process in the presence of an organic solvent and any suitable solvent such as methanol, methylene chloride and the like can be employed. Completion of the reaction is easily determined by the absence of any further H$_2$S by-products given off and said reaction is generally completed within five hours. The amount of sulfide employed is not narrowly critical and need only be that amount sufficient to provide a polysulfide group of at least two sulfur atoms. Normally, amounts of sulfur sufficient to provide a polysulfide group of more than four sulfur atoms are unnecessary and wasteful although such higher amounts can be used if desired. Of course, it is obvious that the preferred reaction conditions for any particular polysulfide silane product can be easily determined by routine experimentation. The solvent if employed can be easily removed by distillation and the polysulfide product recovered by any suitable method. While the polysulfide silanes employable in this invention can be employed in their crude product form, if desired, they may be purified by conventional procedures.

As pointed out above, the starting silanes employed in preparing the polysulfide silanes employable in this invention are those amino substituted mercapto organosilanes disclosed in said concurrently filed U.S. application Ser. Nos. 810,840 (D-9978) and 810,785 (D-10,614).

More specifically such amino substituted mercapto organosilane compounds are those having the formula:

wherein X, R', R, Q, Z, b, n, and t are the same as defined in formula (I) above.

Such amino substituted mercapto organosilanes employable in this invention can be prepared by reacting the novel episulfide substituted organosilanes disclosed in concurrently filed U.S. application Ser. No. 810,851 entitled "Episulfide Substituted Organosilicon Compounds" (D-9972) by T. C. Williams and G. E. Totten the disclosure of which is encompassed herein by reference thereto, with a primary or secondary amine as described in said concurrently filed U.S. application Ser. No. 810,840 (D-9978) and shown by the following equation:

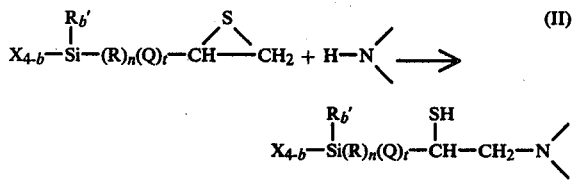

wherein X, R', R, Q, b, n and t are the same as defined in formula (I) above and H—N< is a primary or secondary amine. More specifically said process can be illustrated as follows:

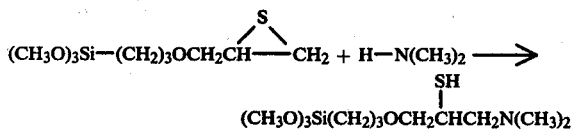

As seen by the above equations the episulfide (or thiiranyl) group on the silane is opened to form the desired mercapto radical (—SH) and provide the bonding to the amino radical derived from the primary or secondary amine reactant, thus resulting in the desired corresponding amino substituted mercapto organo silane products.

Any organic primary or secondary amine which will function as described above in process (II) may be employed to prepare said amino substituted mercapto organosilanes and such amine compounds and/or methods for their preparation are well known in the art. Illustrative examples of such primary and secondary amine reactants include such amines as methylamine, ethylamine, dimethylamine, diethylamine, di-n-butylamine, sec-butylamine, n-octylamine, 2-hydroxyethylamine, bis-(2-hydroxyethyl)amine, 2-methoxyethylamine, 3-hydroxypropylamine, aniline, ortho and para toluidines, ortho and para aminophenols, p-anisidine, o-dimethylaminoaniline, o- and p- chloro anilines, p-acetamidoaniline, benzylamine, o-mercaptoaniline, m-aminophenyltrimethoxysilane, 2-aminopyridine, 5-amino-2-mercaptobenzothiazole, cyclohexylamine, cyclohexylmethylamine, N-methylaniline, 2-naphthylamine, ethylenediamine, diethylene triamine, p-phenylenediamine, oxydianiline, 2-mercaptoethylamine, allylamine, 3-aminocrotononitrile, piperonylamine, piperazine, piperidine, morpholine, 3-(phenylamino)propyltrimethoxysilane, p-aminodiphenylamine, 3-(n-butylamino)propyltrimethoxysilane, and the like.

The process factors involved in forming said amino substituted mercapto organosilanes by the above described process are not critical although certain practical choices may be made as described below.

As pointed out above, process (II) merely involves reacting a corresponding episulfide substituted silane with an organic primary or secondary amine and maintaining the reaction until the episulfide group has been opened to form the desired amino substituted mercapto organosilane. No special catalysts are needed for the process. It is advantageous, however, to carry out the process in the presence of a solvent such as hydrocarbons, ethers, esters, alcohols and mixtures thereof. The amount of solvent used is not narrowly critical, the solvent normally being employed in an amount sufficient to dissolve the reactants involved, although lower or higher amounts can be employed if desired. Of course, it is to be understood that the solvent employed should be chosen so as to not adversely react with the hydrolyzable groups on the starting silane or otherwise adversely affect the desired reaction.

In general, process (II) merely involves mixing both reactants and the solvent and maintaining the resultant solubilized mixture at the reaction temperature until the reaction has been completed. Preferably the amount of organic amine employed is at least stoichiometrically equivalent to the number of episulfide groups of the silane to be reacted or moderately in excess of such amounts, although higher or lower amounts of the organic amine may be employed if desired. The process is generally conducted at atmospheric pressure, although subatmospheric or superatmospheric pressures may be used if desired. It is also preferred that said process be initially conducted in a substantially anhydrous environment due to the reactivity of the reactants and products towards water, thus the process is normally carried out under a dry nitrogen atmosphere.

The reaction temperature in above described process (II) is not narrowly critical and can range from about room temperature up to and including the reflux temperature of the reaction mixture as may be convenient for the operator, the most preferred reaction temperature for any specific reaction being obviously easily determinable by routine experimentation. The process is generally completed within from about one to about four hours, but may be completed faster or take longer depending on such obvious factors as the amounts and types of reactants involved and the solvent and reaction temperature employed. Completion of the reaction is easily determinable e.g. by infrared analysis on a sample of the reaction product for the presence of the mercapto group or by titration of such a sample for the presence of said mercapto group. The solvent employed in the process can be easily removed and the desired amino substituted mercapto organosilane products recovered by any suitable conventional method. For example, the solvent can be removed by stripping at reduced pressures. The amino substituted mercapto organosilanes employable in this invention can be advantageously employed in their crude product form or, if desired, undergo conventional treatment procedures in order to obtain a purer product prior to use.

As pointed out above, said amino substituted mercapto organosilanes are prepared from the novel episulfide substituted organosilanes disclosed in said concurrently filed U.S. application Ser. Nos. 810,851 (D-9972) and 810,785 (D-10,614).

More specifically, such episulfide substituted organosilane compounds are those having the formula:

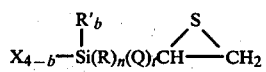

wherein X, R', R, Q, b, n and t are the same as defined in formula (I) above.

Preferably the episulfide substituted organosilanes are prepared by reacting a corresponding epoxide containing silane with thiourea as shown by the following equation:

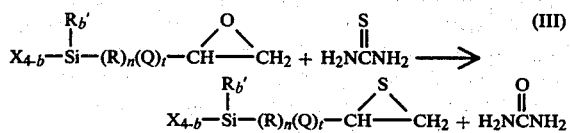

wherein X, R', R, Q, b, n and t are the same as defined above. More specifically said process can be illustrated as follows:

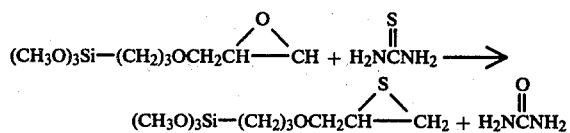

Alternatively the episulfide substituted organosilanes can also be prepared by reacting a corresponding epoxide containing silane with a metal thiocyanate salt as shown by the following equation:

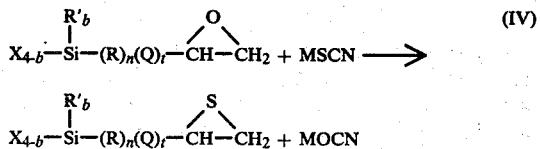

wherein X, R', R, Q, b, n and t are the same as defined above and M is a metal such as an alkali metal. More specifically said process may be illustrated as follows:

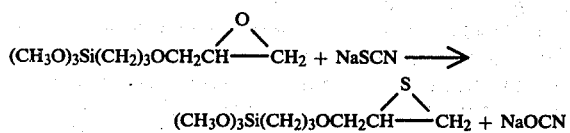

As seen by the above equations the oxygen atom of the epoxide radical of the starting material is replaced by the sulfur atom of the thiourea or metal thiocyanate salt to form the desired episulfide radical, thus resulting in the desired corresponding episulfide substituted silane products.

The reaction compounds, i.e. epoxide containing silanes, thiourea, or metal thiocyanate salts and/or methods for their production, which can be used in the above described processes (III) and (IV) are well known in the art. Illustrative metal thiocyanate salt starting materials include e.g. the alkali metal thiocyanates such as NaSCN, KSCN and the like.

The process factors involved in forming the episulfide substituted organosilanes by either of the above two described preferred methods (III) and (IV) are not critical although certain practical choices may be made as described below;

As pointed out above, the two methods of preparation merely involve reacting a corresponding epoxide containing silane with thiourea (Process (III)) or a metal thiocyanate salt (Process (IV)) and maintaining the reaction until the oxygen atom of the epoxide starting material has been replaced with the sulfur atom of the thiourea or metal thiocyanate salt to form the desired episulfide substituted organosilane.

No special catalysts are needed for either process. It is advantageous, however, to employ a polar solvent. Suitable solvents include aliphatic alcohols such as methanol, ethanol, n-propanol, t-butanol and the like. The amount of solvent used is not narrowly critical the solvent normally being employed in an amount sufficient to dissolve the reactants involved, although lower or higher amounts can be employed if desired. Of course, it is to be understood that the solvent employed should be chosen so as to not adversely react with the hydrolyzable groups on the starting silane or otherwise adversely affect the desired reaction.

In general, both processes (III) and (IV) described above merely involve mixing both reactants and the solvent and maintaining the resultant solubilized mixture at the reaction temperature until the reaction has been completed. Any convenient order of mixing can be employed. In both processes stoichiometric amounts of reactants can be used, while it may sometimes be advantageous to use an excess of urea or metal thiocyanate in order to increase the yield or the reaction rate. Both processes are generally conducted at atmospheric pressure, although subatmospheric or superatmospheric pressures may be used if desired. It is also preferred that said processes (III) and (IV) be initially conducted in a substantially anhydrous environment due to the reactivity of the reactants and products towards water thus both processes are normally carried out under a dry nitrogen atmosphere.

The reaction temperature for both processes (III) and (IV) are not narrowly critical and can range from about room temperature up to and including the reflux temperature of the reaction mixture as may be convenient for the operator, the most preferred reaction temperature for any specific reaction being obviously easily determinable by routine experimentation. Both processes (III) and (IV) are generally completed within from about one to about four hours but may be completed faster or take longer depending on such obvious factors as the amounts and types of reactants involved, and the solvent and reaction temperature employed. Completion of said reactions is easily determinable, e.g. by the cessation of any further formation of undesirable solid urea or cyanate salt by-product. The solvent employed and the by-products of said preferred processes (A) and (B) can be easily removed, and the desired normally liquid episulfide substituted silane products recovered by any suitable conventional method. For example, the solvent can be removed by distillation and the solid by-products by filtration, centrifuging and the like. While the episulfide substituted organosilanes can be advantageously employed in their crude product form, or they can, if desired, undergo conventional treatment procedures in order to obtain a purer product prior to use.

Illustrative polysulfide silanes that may be derived from their corresponding amino substituted mercapto organosilane starting materials include

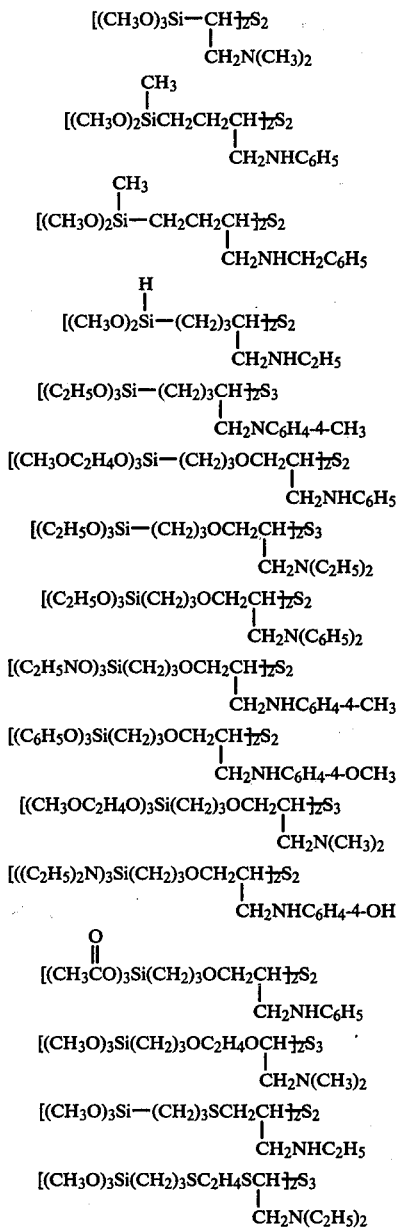

and the like.

Alternatively the silicon coupling agent compositions of matter employable in this invention include polysulfide siloxanes. Illustrative of such polysulfide siloxanes are those consisting essentially of siloxy units having the formula

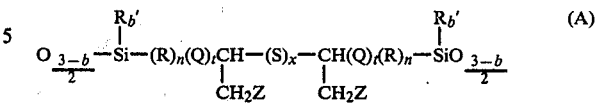

wherein R', R, Q, Z, n, t, b and x are the same as defined above; as well as polysulfide siloxane copolymers consisting of at least one siloxy unit represented by formula (A) above and at least one siloxy unit represented by the formula:

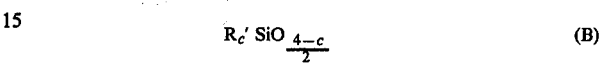

wherein R' is the same as defined in formula (A) above, and wherein c has a value of from 0 to 3 inclusive.

For example, the polysulfide silanes of this invention can be hydrolyzed and condensed in the conventional manner, either alone or together with other hydrolyzable silanes to produce siloxanes consisting essentially of the siloxy units of formula (A) above or copolymer siloxanes consisting essentially of siloxy units of formula (A) above and formula (B) above. When the polysulfide silanes of this invention are cohydrolyzed and condensed with other conventional hydrolyzable silanes, the siloxanes produced are copolymers composed essentially of siloxy units of formula (A) above and formula (B) above. Illustrative conventional hydrolyzable silanes are those of the formula $R'_c$-Si-$X_{4-c}$ wherein R' and c are the same as defined above and X is a hydrolyzable group such as an alkoxy radical, e.g. methoxy.

Thus, in general the polysulfide siloxanes must contain at least one siloxy unit such as

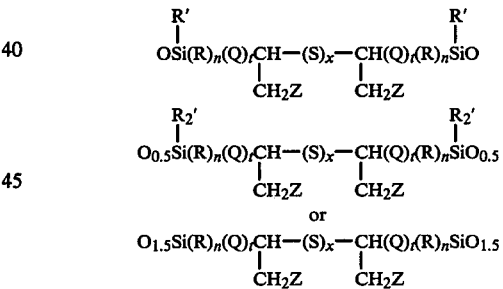

may contain one or more siloxy units, such as $R'_3SiO_{0.5}$, $R'_2SiO$, $R'SiO_{1.5}$, or $SiO_2$, wherein Z, Q, R, R', t, n and x are the same as defined above. Of course, it is understood that the siloxanes can also contain a minor amount of hydrolyzable groups if complete hydrolysis is not obtained.

The hydrolysis and condensation of the polysulfide silanes of this invention are not critical and can be carried out in any conventional manner, and such procedures are well known in the art. Alternatively, the polysulfide siloxanes of this invention can also be prepared by reacting a corresponding amino-substituted mercapto organosiloxane in the same manner as described above for producing the polysulfide silanes of this invention. However, it is to be understood that when such alternative method is employed the siloxanes of this invention can contain hydrolyzable end blocked siloxy units if the starting materials contain same as well as minor amounts of siloxy units having unreacted amino and mercapto substituted organo groups if the reaction is incomplete.

Elemental analysis, $C^{13}$ nuclear magnetic resonance spectroscopy and proton nuclear magnetic resonance spectroscopy confirmed that the polysulfide silane compositions of matter of this invention consist essentially of compositions having the general formula (I) employed herein above. It is to be understood, of course, that since the amino substituted mercapto organo-silicon starting materials may contain minor amounts of mercapto groups bonded directly to the ($CH_2$) group of said formula (I) and like amounts of the amino radical bonded directly to the (CH) group of said formula (I) then the polysulfide silicon compositions of this invention may also contain minor amounts (normally not more than 10%) of the polysulfide groups bonded directly to said ($CH_2$) group and like amounts of the amino radical bonded directly to said (CH) group.

The function of a silicon coupling agent to provide a strong chemical bridge between the inorganic substrate and the organic polymer employed is well known in the art. It is of course understood that for effective coupling action in a particular polymer substrate composite, it is necessary to select the appropriate coupling agent, i.e. one which is suitable reactive towards both the polymer component and the substrate component for each particular polymer-substrate composite considered. Thus, while there may be more than one appropriate coupling agent for a particular polymer substrate composite, a given coupling agent may not be appropriate for all polymer composites. However, the selection of the most preferred coupling agent for any particular polymer composite is well within routine experimentation.

The particular manner of compounding the polymer composite articles of manufacture of this invention as well as the various amounts of ingredients employed are not critical and merely depend on the particular finished polymer composite desired along with the ultimate end use for which it is to be employed and such steps as compounding, heating, crosslinking or vulcanizing, and the like, may be conducted in any conventional manner heretofore employed in preparing conventional polymer composites such as thermoplastic resin composites, thermoset, resin composites, vulcanized rubber composites, and the like.

For example, in the case of conventional polymer-filler type composites such as vulcanized rubber articles the polysulfide organosilicon coupling agents and/or solubilized solutions thereof can be added to the vulcanizable rubber polymer batch together with the substrate filler and various other additives during mill or banbury mixing. Alternatively, the substrate fillers or vulcanizable rubber polymers can be treated (coated) with the polysulfide organosilicon coupling agents and/or solubilized solutions thereof prior to incorporation into the rubber polymer or filler master batch. Generally, it is preferred to employ the polysulfide organosilicon coupling agents neat, mix them with the substrate filler, preferably a silica or metal silicate filler, and add the mixture to the polymer batch prior to the incorporation of the other conventional additives normally employed in such polymer filled composites. Moreover, if desired, the polysulfide organosilicon coupling agents can be taken up (absorbed) on any suitable conventional microporous carrier, e.g. Microcel E, a calcium silicate, prior to use to form a dry free flowing powder concentrate. Such microporous carriers, in the amounts normally used, do not affect the properties of the composite product articles and the free flowing powder concentrate provides convenience in handling and metering of the coupling agent. As pointed out above, the particular procedures involved and amount ratios of the components employed are all within the knowledge of one skilled in the art and are left to the choice of the operator. More specifically, however, the preferred polymer composite articles of this invention are vulcanized rubber articles. Thus, in general, the amount of polysulfide organosilicon coupling agent employed in the vulcanized rubber composites of this invention will normally range from about 0.1 to about 20 parts by weight (preferably from about 0.2 to about 10 parts by weight) per 100 parts by weight of inorganic substrate filler employed although higher or lower amounts may be employed if desired. Of course, the amount of inorganic substrate filler employed merely depends on the desired rubber product end use and may range from about 5 up to as high as 300 parts by weight or higher per 100 parts by weight of vulcanized rubber polymer employed. The vulcanizable rubber compound is normally vulcanized in the presence of conventional sulfur or peroxide curatives that are well known in the art. For example, a conventional sulfur curative may include per 100 parts by weight of vulcanizable rubber polymer from about 0.5 to 4 parts by weight of sulfur, about 2 to 5 parts by weight of zinc oxide, and about 0.2 to 3 parts by weight of accelerators (e.g. diphenylguanidine); while a conventional peroxide curative generally may include per 100 parts by weight of vulcanizable rubber polymer from about 1 to about 8 parts by weight of an organic peroxide e.g. dicumyl peroxide, $\alpha,\alpha'$-bis(t-butyl peroxy) diisopropylbenzene, and the like. The vulcanization procedure of a rubber polymer is well known in the art and in general may be conducted at temperatures ranging from 260° F. to about 360° F. although lower or higher temperatures may be employed if desired. Of course, it is obvious that if desired the vulcanized rubber composites of this invention may contain any of the conventionally additional ingredients such as extenders, carbon blacks, processing oils, plasticizers, antioxidants, lubricants, accelerators, retardants, coloring pigments and dyestuffs and the like, normally employed in conventional vulcanized rubber composites and such is well within the knowledge of one skilled in the art.

In the case of conventional rubber, thermoplastic or thermoset polymer laminate type composites wherein e.g. the inorganic substrate is glass fibers, it is generally preferred to pretreat (coat) the inorganic substrate with the polysulfide organosilicon coupling agent prior to bonding with the organic polymer employed although the coupling agent and organic polymer can be deposited together on the substrate and then bonded or the polymer first treated with the coupling agent and then coated onto the substrate and bonded, it desired. The polysulfide organosilicon coupling agent may be employed neat, although it is generally preferred to employ a solubilized solution of the coupling agent by employing an appropriate solvent such as those discussed above, and more preferably to employ an aqueous composition of the polysulfide organosilicon coupling agent, especially the silane coupling agents. The production of such polymer laminate type composites is well known in the art. The various amounts of compounds employed of course merely depend upon the polysulfide organosilicon coupling agent employed, the surface area to be covered, the organic polymer to be bonded to the substrate and the like. Moreover, the method of coating the substrate is not critical and the coupling agent can be sprayed, brushed, poured, or rolled on to the surface to the substrate and the like, or alternatively the substrate can be dipped into a solvent solution or aqueous composition of the coupling agent. Likewise, the temperature at which the bonding reaction is carried out can be varied over a wide range depending upon the specific compounds employed. In general, heat temperatures will generally be in the range of about 100° C. to about 350° C. or higher, although if desired the bonding between the substrate, coupling agent and organic polymer may also be carried out by the use of ultra-violet radiation, X-rays, and the like. Of course, it is obvious that such polymer laminate type composites if desired may contain any of the conventional additional ingredients normally employed in conventional polymer-laminate articles such as catalysts, antioxidants, pigments, and the like.

Accordingly, another aspect of this invention is directed to an inorganic substrate as defined above treated with polysulfide organosilicon coupling agent as defined above. When employed aqueous compositions of the coupling agent generally comprise from about 0.1 to about 20 parts by weight of the polysulfide organosilicon coupling agent and from about 99.9 to about 80 parts by weight of water. Such aqueous compositions may be in the form of solutions, dispersions or emulsions and may be especially suitable for use as sizing and finishing agents in the glass fiber industry. If desired the polysulfide organosilicon coupling agent can be employed in the form of a water-soluble solvent solubilized solution. Generally, it is preferred to employ aqueous compositions of a polysulfide organosilane coupling agent. Of course, it is to be understood that since the polysulfide organosilicon coupling agents contain hydrolyzable groups (e.g. alkoxy radicals) the aqueous compositions of such include and encompass, the hydrolyzates, partial hydrolyzates, condensates and partial condensates of said silicon coupling agents. The treatment or coating of the inorganic substrate with said aqueous compositions is conventional as discussed above.

Thus, it will be readily apparent to those skilled in the art that the polysulfide organosilicon coupling agents employed in this invention lend themselves to any conventional process where organic polymers are to be bonded to inorganic substrates and thus to the formation of a wide range of polymer composite articles of manufacture such as filled vulcanized rubber products, filled thermoset and thermoplastic products, organic polymer-substrate (e.g. glass fibers) laminate products, and the like, heretofore prepared with conventional silane coupling agents.

Evidence of action by a coupling agent is manifested through changes in composite properties away from the values displayed in the absence of the agent and the properties which may be favorably altered are many and varied. In elastomeric and resinous composites the improved effects attributable to the instant invention are often seen in terms of its increased resistance to deforming forces and abrasion resistance and in decreased hysteresis losses in flexure. For example, the reactivity and/or bonding between the organic polymer, inorganic substrate and polysulfide organosilicon coupling agent of this invention is demonstrated by improved physical properties in the finished polymer composite product, such as tensile modulus, and the like as compared to the physical properties of the same finished composite product prepared without the use of the polysulfide organosilicon coupling agent. Likewise, while the polysulfide organosilicon "coating" per se on the pretreated inorganic substrate articles of this invention is not measurable, its presence is also confirmed by such improved physical properties in the finished polymer composite prepared with such pretreated substrates as compared to the same finished product prepared with an untreated substrate and without the use of any polysulfide organosilicon coupling agent.

The following examples are illustrative of the present invention and are not to be regarded as limitative. It is to be understood that all parts, percentages and proportions referred to herein and in the claims are by weight unless otherwise indicated. Tensile modulus is defined as tensile stress in pounds per square inch of original cross-sectional area necessary to produce a given extension in a composite specimen, usually 300% of the unstressed length.

EXAMPLE 1

Into a 1-liter, 3-neck flask equipped with a magnetic stirrer, thermometer, and a reflux condenser having a nitrogen by-pass for carrying out the reaction under a nitrogen atmosphere were charged about 269.6 grams of distilled glycidoxypropyltrimethoxysilane, about 86.9 grams of thiourea and about 312.2 grams of methanol. The stirred solubilized reaction mixture was boiled at reflux (about 65° C.) for one hour, then cooled and the methanol solvent stripped out under reduced pressure. The reaction product mixture was then dissolved in diethyl ether and then washed with water to remove the precipitated urea by-product and any unreacted thiourea. The ether solution was then dried with anhydrous magnesium sulfate, filtered, and the ether stripped off under reduced pressure to yield about 234.4 grams of the desired fluid 1,2-epithio-4-oxa-7-trimethoxysilyl heptane crude product which has the formula

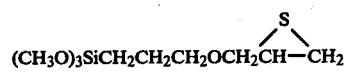

The structure of said crude product was confirmed by infrared absorption spectroscopy, proton magnetic resonance spectroscopy and $C^{13}$ magnetic resonance spectroscopy analysis, as well as by chemical analysis for methoxy and elemental silicon content.

About 40 grams of said crude product were then distilled through a 1-foot Vigreaux column at about 0.18 mm Hg. to yield about 35.6 grams of yellow-white viscous 1,2-epithio-4-oxa-7-trimethoxysilyl heptane oil having boiling points of about 95° C. at 0.07 mm Hg. and about 108° C. at 0.18 mm Hg. and a refractive index of $n_D^{20}=1.460$. The structure for said distilled 1,2-epithio-4-oxa-7-trimethoxysilyl heptane product was confirmed by $C^{13}$ nuclear magnetic resonance spectroscopy, laser Raman spectroscopy and vapor phase chromatography.

EXAMPLE 2

Preparation of 1-dimethylamino-2-mercapto-4-oxa-7-(trimethoxysilyl) heptane

In a 500 cc flask equipped with thermometer, condenser, magnetic stirrer, heater, $N_2$ atmosphere and dropping funnel were placed 50.0 parts by weight of hexane plus 7.0 parts by weight of dimethylamine. While gently warming to about 46° C., 25.2 parts by weight of a crude 1,2-epithio-4-oxa-7-trimethoxysilyl heptane product, prepared as described in Example 1 above, was added dropwise. The mixture was boiled at reflux (57° C.) for three hours, cooled and the solvent stripped under reduced pressure. A slight turbidity in the mixture, apparently due to polymer formation was removed by filtration. Analysis by $C^{13}$ and proton nuclear magnetic resonance spectroscopy and by chemical titrations for mercapto and amino content of the product confirmed that an amino substituted mercapto organosilane having the formula $$(CH_3O)_3Si(CH_2)_3OCH_2CH(SH)CH_2N(CH_3)_2$$

was produced in an 80% yield (based on titration for the mercapto group).

EXAMPLE 3

Preparation of bis-[1-dimethylamino-4-oxa-7-(trimethoxysilyl)-2-heptane]disulfide.

In a 25 cc flask equipped with a thermometer, condenser, magnetic stirrer, heater, nitrogen sparge tube to facilitate removal of hydrogen sulfide, and a dropping funnel were placed 1.15 parts by weight of elemental sulfur (Niagara Rubbermakers #104) and 50.0 parts by weight of methylene chloride. Nitrogen was bubbled very gently into the reaction mixture and with stirring 25.0 parts by weight of 1-dimethylamino-2-mercapto-4-oxa-7-(trimethoxysilyl) heptane (prepared as described in Example 2) were added dropwise at ambient temperature. The reaction mixture was stirred at ambient temperature for one hour and then boiled at reflux for four hours, cooled and the solvent stripped off under reduced pressure. Analysis by $C^{13}$ nuclear magnetic resonance spectroscopy and by chemical titrations for amino and residual thiol groups as well as the sulfur to silicon ratio of the crude product confirmed that a polysulfide silicon compound having the formula

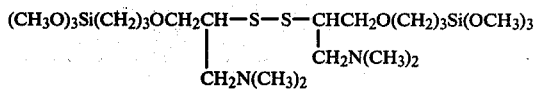

was produced in a 93% yield.

EXAMPLES 4 TO 8

A variety of polysulfide silane compounds were prepared according to the general procedure of Example 3 above using either a 1-dimethylamino-2-mercapto-4-oxa-7-(trimethoxysilyl) heptane product prepared as described in Example 2 above (i.e. the starting silane material in Example No. 4 of TABLE I below), or a 1-piperidino-2-mercapto-4-oxa-7-(trimethoxysilyl) heptane product prepared according to the general procedure of Example 2 above and as described in Example 4 of applicants' said concurrently filed U.S. application Ser. No. 810,840 (D-9978) (i.e. the starting silane material in Examples Nos. 5 and 6 of TABLE I below), or a 1-anilino-2-mercapto-4-oxa-7-(trimethoxysilyl) heptane product prepared according to the general procedure of Example 2 above and as described in Example 6 of applicants' said concurrently filed U.S. application Ser. No. 810,840 (D-9978) (i.e. the starting silane material in Examples Nos. 7 and 8 TABLE I below). Analysis by $C^{13}$ and proton nuclear magnetic resonance spectroscopy as well as titration for residual thiol groups confirmed that the polysulfide products of each example were all obtained in greater than 95% yields.

TABLE I

| Ex. No. | Amino, Mercapto Silane | Parts by Wt. | Sulfur* (Parts By Wt.) | Solvent (Parts By Wt.) | Polysulfide Silane Product |
|---|---|---|---|---|---|
| 4 | (CH$_3$O)$_3$Si(CH$_2$)$_3$OCH$_2$CH(SH)CH$_2$N(CH$_3$)$_2$ | 25.0 | 2.3 | Methylene Chloride (50.0) | [(CH$_3$O)$_3$Si(CH$_2$)$_3$OCH$_2$CH(CH$_2$N(CH$_3$)$_2$)]$_2$S$_3$ |
| 5 | (CH$_3$O)$_3$Si(CH$_2$)$_3$OCH$_2$CH(SH)CH$_2$N(piperidino) | 25.8 | 1.1 | Methanol (50.0) | [(CH$_3$O)$_3$Si(CH$_2$)$_3$OCH$_2$CH(CH$_2$N(piperidino))]$_2$S$_2$ |
| 6 | (CH$_3$O)$_3$Si(CH$_2$)$_3$OCH$_2$CH(SH)CH$_2$N(piperidino) | 20.0 | 1.7 | Methylene Chloride (100.0) | [(CH$_3$O)$_3$Si(CH$_2$)$_3$OCH$_2$CH(CH$_2$N(piperidino))]$_2$S$_3$ |
| 7 | (CH$_3$O)$_3$Si(CH$_2$)$_3$OCH$_2$CH(SH)CH$_2$NH(phenyl) | 29.8 | 1.1 | Methanol (50.0) | [(CH$_3$O)$_3$Si(CH$_2$)$_3$OCH$_2$CH(CH$_2$NH(phenyl))]$_2$S$_2$ |
| 8 | (CH$_3$O)$_3$Si(CH$_2$)$_3$OCH$_2$CH(SH)CH$_2$NH(phenyl) | 15.3 | 1.2 | 50% Methanol/ 50% Methylene Chloride (200.0) | [(CH$_3$O)$_3$Si(CH$_2$)$_3$OCH$_2$CH(CH$_2$NH(phenyl))]$_2$S$_3$ |

*Elemental Sulfur (Niagara Rubber maker #104)

EXAMPLES 9–15

A variety of silica-filled rubber compounds were prepared using the formulations of TABLE II and the same procedure. The silane coupling agents employed were the polysulfide silane products of Examples 3 to 8 above and are identified as Silanes A to F respectively in TABLE III below. Thus, said Silanes A to F have the structural formulas given for the products in above Examples 3 to 8 respectively.

TABLE II

| Formulation | (Parts by Weight) |
|---|---|
| Styrene-Butadiene Rubber[1] | 100 |
| Silica Filler[2] | 35 |
| Silane Coupling Agent | Varied* |
| Softener Oil[3] | 8.0 |
| BBS[4] | 1.2 |
| DOTG[5] | 2.5 |
| Sulfur | 1.6 |
| Zinc Oxide | 4.0 |
| Stearic Acid | 1.0 |

[1]SBR 1502
[2]Precipitated silica (Hi-Sil 233, Trademark of PPG Industries, Inc.)
[3]Sundex 790, an aromatic processing oil (Trademark of Sun Oil Co.)
[4]N-t-butyl-2-benzothiazole sulfenamide
[5]Di-ortho-tolyl guanidine
*As shown in Table III below.

Each formulation was prepared using a 2 roll rubber mill having a roll temperature of about 130° F. The rubber polymer was charged to the rubber mill and milled until smooth and plastic. Then a small portion of the filler was added to the polymer band, followed by the addition of more filler along with the silane coupling agent which was added dropwise and concurrently with the filler. After all the silane and about half of the filler had been added the softening oil was added concurrently with the remainder of the filler. After an intimate milled mixture of the styrenebutadiene rubber, silica filler, silane coupling agent and softener was obtained, the sulfur, accelerators and other ancillary ingredients were added and the mixture further milled until an intimate dispersion was obtained. After storing at ambient room conditions for at least 16 hours, the mixture was remilled until plastic. Molded preformed sheets were cut from the remilled mixture of each formulation and then vulcanized in the same manner in a mold under pressure at 320° F. to 340° F. After resting at ambient room conditions for at least 16 hours the physical properties of the vulcanized molded rubber composites were then measured and the results recorded as shown in TABLE III.

TABLE III

| Ex. No. | Silane Coupling Agent (Parts by Wt.) | 300% Tensile Modulus (psi)[1] | Tensile Strength (psi)[1] | Elongation at Break (%)[1] | Tear Strength (psi)[2] |
|---|---|---|---|---|---|
| 9 | Control-No Silane | 320 | 2480 | 800 | 160 |
| 10 | Silane A (1.86) | 510 | 3660 | 720 | 340 |
| 11 | Silane B (1.90) | 490 | 3860 | 760 | 240 |
| 12 | Silane C (1.97) | 470 | 3660 | 730 | 230 |
| 13 | Silane D (4.60) | 520 | 3270 | 730 | 240 |
| 14 | Silane E (1.98) | 450 | 3600 | 750 | 220 |
| 15 | Silane F (4.60) | 520 | 3100 | 700 | 230 |

[1]Tested in compliance with ASTM D-412.
[2]Tested in compliance with ASTM D-624.

The above data demonstrates a significant improvement in the tensile modulus of the silane containing vulcanized rubber compound of Examples 10 to 15 over the non-silane containing vulcanized rubber compound of control Example 9.

As noted above, the polysulfide silane compositions of matter are extremely effective coupling agents and thus offer exceptional promise in the production of filled-vulcanized rubber articles such as tires, gaskets, hoses and other conventional mechanical rubber goods.

Various modifications and variations of this invention will be obvious to a worker skilled in the art and it is to be understood that such modifications and variations are to be included within the purview of this application and the spirit and scope of the appended claims.

What is claimed is:

1. An inorganic substrate treated with a polysulfide silicon coupling agent selected from the class consisting of (i) polysulfide silanes having the formula

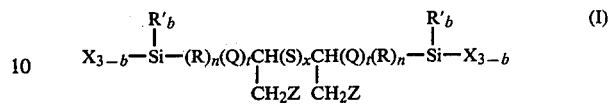

wherein R' is hydrogen or a monovalent radical selected from the class consisting of hydrocarbon radicals and substituted hydrocarbon radicals;

wherein X is a hydrolyzable radical selected from the class consisting of alkoxy, aryloxy, acyloxy, secondary amino and aminooxy radicals;

wherein R is a divalent bridging group selected from the class consisting of hydrocarbon radicals, groups of the formula —R"OR"— and groups of the formula —R"SR"— wherein R" is a divalent hydrocarbon radical.

wherein Q is an oxygen atom or a sulfur atom;

wherein Z is a monovalent organic amino radical the nitrogen atom of which is directly bonded to the carbon atom of the (CH$_2$) group of the above formula;

wherein n has a value of 0 or 1 and t has a value of 0 or 1, with the proviso that when n is 0, then t is 0; and wherein b has a value of 0 to 2, and x has a value of 2 to 4; (ii) polysulfide siloxane homopolymers consisting essentially of siloxy units having the formula

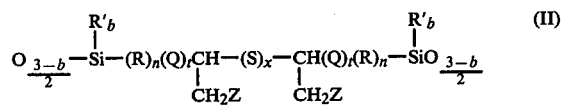

wherein R', R, Q, Z, n, t, b and x are the same as defined above; and (iii) polysulfide siloxane copolymers consisting essentially of at least one siloxy unit represented by formula (II) above and at least one siloxy unit represented by the formula

wherein R' is the same as defined in formula (II) above, and wherein c has a value of from 0 to 3 inclusive.

2. An inorganic substrate as defined in claim 1 wherein the substrate is a siliceous reinforcing material.

3. An inorganic substrate as defined in claim 2 wherein the polysulfide silicon coupling agent is a polysulfide silane having the formula

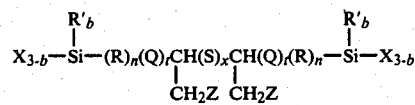

4. An inorganic substrate as defined in claim 3 wherein R' is an alkyl radical, wherein X is an alkoxy radical, wherein R is an alkylene or alkyleneoxyalkylene radical, wherein n is 1, and t is 0, wherein Z is an organic amino radical of the formula $-NZ^1Z^2$ wherein $Z^1$ and $Z^2$ are taken individually and $Z^1$ is an organic radical selected from the class consisting of alkyl, aryl, aralkyl, alkaryl and haloaryl radicals, hydroxy substituted alkyl, aryl, aralkyl and alkaryl radicals, alkoxy substituted alkyl, aryl, aralkyl and alkaryl radicals, mercapto substituted alkyl, aryl, aralkyl and alkaryl radicals, and hydrolyzable silyl substituted alkyl, aryl, aralkyl and alkaryl radicals; and wherein $Z^2$ is hydrogen or a $Z^1$ radical as defined above.

5. An inorganic substrate as defined in claim 4 wherein b is 0 and wherein R is an alkyleneoxyalkylene radical.

6. An inorganic substrate as defined in claim 5 wherein X is a methoxy radical and wherein R is a propyleneoxymethylene radical.

7. An inorganic substrate as defined in claim 2 wherein the polysulfide silicon coupling agent is a polysulfide siloxane homopolymer consisting essentially of siloxy units having the formula

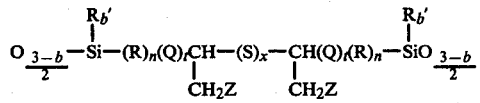

8. An inorganic substrate as defined in claim 7 wherein R' is an alkyl radical, wherein R is an alkylene or alkyleneoxyalkylene radical, and wherein n is 1 and t is 0.

9. An inorganic substrate as defined in claim 8 wherein R is a propyleneoxymethylene radical and wherein Z is an organic amino radical of the formula $-NZ^1Z^2$ wherein $Z^1$ and $Z^2$ are taken individually and $Z^1$ is an organic radical selected from the class consisting of alkyl, aryl, aralkyl, alkaryl and haloaryl radicals, hydroxy substituted alkyl, aryl, aralky and alkaryl radicals, alkoxy substituted alkyl, aryl, aralkyl and alkaryl radicals, mercapto substituted alkyl, aryl, aralkyl and alkaryl radicals, amino substituted alkyl, aryl, aralkyl and alkaryl radicals, and hydrolyzable silyl substituted alkyl, aryl, aralkyl and alkaryl radicals; and wherein $Z^2$ is hydrogen or a $Z^1$ radical as defined above.

10. An inorganic substrate as defined in claim 2 wherein the polysulfide silicon coupling agent is a polysulfide siloxane copolymer consisting essentially of at least one siloxy unit of the formula

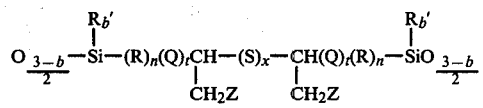

and at least one siloxy unit represented by the formula

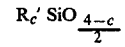

11. An inorganic substrate as defined in claim 10 wherein R' is a monovalent hydrocarbon radical, wherein R is an alkylene or alkyleneoxyalkylene radical and wherein n is 1, and t is 0.

12. An inorganic substrate as defined in claim 11 wherein R is a propyleneoxymethylene radical and wherein Z is an organic amino radical of the formula $-NZ^1Z^2$ wherein $Z^1$ and $Z^2$ are taken individually and $Z^1$ is an organic radical selected from the class consisting of alkyl, aryl, aralkyl, alkaryl and haloaryl radicals, hydroxy substituted alkyl, aryl, aralkyl and alkaryl radicals, alkoxy substituted alkyl, aryl, aralkyl and alkaryl radicals, mercapto substituted alkyl, aryl, aralkyl and alkaryl radicals, amino substituted alkyl, aryl, aralkyl and alkaryl radicals, and hydrolyzable silyl substituted alkyl, aryl, aralkyl and alkaryl radicals; and wherein $Z^2$ is hydrogen or a $Z^1$ radical as defined above.

13. An inorganic substrate as defined in claim 2 wherein the siliceous reinforcing material is selected from the class consisting of silica fillers, metal silicate fillers and glass fibers.

14. An inorganic substrate as defined in claim 2 wherein the episulfide substituted organosilicon coupling agent is employed in the form of a solubilized solution.

15. An inorganic substrate as defined in claim 2, wherein the episulfide substituted organosilicon coupling agent is employed is employed in the form of an aqueous composition.

* * * * *